United States Patent [19]

Hammett et al.

[11] Patent Number: 5,352,200
[45] Date of Patent: Oct. 4, 1994

[54] NON-REUSABLE SYRINGE WITH NEEDLE GUARD

[76] Inventors: Roy Hammett, 16103 Carden Dr., Odessa, Fla. 33556; Eric J. Sundsvold, 5121 Ironton Way, Englewood, Colo. 80111

[21] Appl. No.: 103,046

[22] Filed: Jul. 28, 1993

Related U.S. Application Data

[60] Division of Ser. No. 985,301, Dec. 4, 1992, abandoned, which is a continuation-in-part of Ser. No. 802,628, Dec. 5, 1991, Pat. No. 5,181,912.

[51] Int. Cl.$^5$ .............................................. A61M 5/00
[52] U.S. Cl. .................................... 604/110; 604/192
[58] Field of Search ............... 604/110, 218, 263, 193, 604/194, 196, 192, 187

[56] References Cited

U.S. PATENT DOCUMENTS

| | | | |
|---|---|---|---|
| 4,317,446 | 3/1982 | Ambrosio et al. | 604/197 X |
| 5,084,017 | 1/1992 | Maffetone | 604/110 |
| 5,084,027 | 1/1992 | Bernard | 604/192 |

FOREIGN PATENT DOCUMENTS

| | | | |
|---|---|---|---|
| 0848081 | 9/1952 | Fed. Rep. of Germany | 604/193 |
| 2401665 | 4/1979 | France | 604/193 |

*Primary Examiner*—John D. Yasko
*Attorney, Agent, or Firm*—Dennis H. Lambert

[57] ABSTRACT

A disposable hypodermic syringe having a barrel with an adapter on one end for attachment of a needle, and a piston and plunger reciprocable in the barrel. The plunger has a longitudinally extending hollow bore therein and is removable from the barrel and lockable on the adapter in enclosing relationship to the needle to serve as a needle guard. In one form of the invention, the piston and plunger are automatically separable upon use to prevent reuse of the syringe.

11 Claims, 7 Drawing Sheets

NON-REUSABLE SYRINGE WITH NEEDLE GUARD

This application is a division of Ser. No. 07/985,301, filed Dec. 4,1992, now abandoned, which is a continuation-in-part of copending application Ser. No. 07/802,628, filed Dec. 5, 1991, and entitled Non-Reusable Syringe now U.S. Pat. No. 5,181,912.

FIELD OF THE INVENTION

This invention relates generally to hypodermic syringes, and more particularly, to a hypodermic syringe having a part that is removable after use to serve as a needle guard.

BACKGROUND OF THE INVENTION

It is frequently necessary to use hypodermic syringes for intravenous administration of fluids, or to withdraw fluids from the veins of a person during the course of treatment of an illness, or in routine diagnostic examinations. Hypodermic syringes used for this purpose are generally disposable, and are intended to be discarded after a single use by trained medical personnel.

However, unless they are properly disposed of, these used syringes present a serious health hazard to persons subsequently handling them. For instance, if the needle is left intact and is not sheathed in a protective guard, it is possible that someone could be accidentally pricked with the needle during subsequent handling of it. If the syringe has been used to make an injection or withdraw body fluid from a person having an infectious disease, the consequences could be very serious to someone accidentally pricked with the needle.

One of the more serious concerns of health care workers is the danger of becoming accidentally infected with HIV-infected blood or other materials. Acquired Immune Deficiency Syndrome (AIDS) is now recognized as an epidemic of global proportion. In addition, there is an increasing recognition of a broad spectrum of severe HIV-associated diseases, including pneumonia, endocarditis, and pulmonary tuberculosis.

Medical and rescue personnel are aware of these risks, and when possible, take precautions to avoid unnecessary exposure or contact with infectious materials.

However, if a used syringe has been left intact and not properly disposed of, medical and rescue personnel, custodial workers, and others, are exposed to the danger of being accidentally pricked with the contaminated needle in spite of the precautions that they might normally take. Such a needle could be mingled with soiled linens, bandages or other materials, and when these materials are gathered for disposal, the needle has the distinct potential of penetrating the skin of anyone handling the materials.

To prevent such accidents from occurring, the needles should be broken from the used syringes, and/or encased in a protective sheath, and devices have been provided in the prior art for accomplishing this.

For instance, needles have been joined to the syringe body through frangible connections so that the doctor, nurse or other medical personnel can easily break the needle from the syringe after it is used. Unfortunately, this is not always done during the urgency of medical treatment, or if it is, there still remains an exposed needle body.

Similar shortcomings exist with respect to guards or sheaths that have been provided to encase the used needle. Such guards generally comprise separate sleeves or cap members that enclose the needle before it is used and which must be removed and set aside during use of the syringe. It is intended that after use of the needle, the guard will again be placed over the needle. However, the guard may become misplaced during the medical procedure being performed and therefore not available for reuse. Even if it is not misplaced, the person responsible for safe handling of the syringe may not have the time, or take the time, to retrieve the guard and place it over the needle.

A further problem exists with respect to syringes that are not properly disposed of or rendered inoperative after use. Used syringes of conventional construction are capable of reuse, and are thus liable to spread infectious diseases.

Although the medical community has long used disposable syringes a single time and then disposed of the used syringe, these syringes are sometimes stolen from hospitals, or from medical equipment suppliers, or are not properly disposed of after being used by authorized personnel, and ultimately come into the possession of drug abusers. Intravenous drug abusers consistently use the same syringe over-and-over again and share them with other drug abusers. This practice has led to the rapid spread of HIV, Hepatitis and other infectious diseases in the illicit drug use population.

Intravenous drug use is believed to account for most AIDS-related diseases in heterosexual men and women. This disease may also be transmitted to the children of infected adults, and to the sex partners of the infected persons, or to others, such as medical workers and rescue personnel, who may be inadvertently exposed to the blood of the infected person.

As AIDS-related diseases continue to grow, it is becoming increasingly more important to control the means by which these diseases are transmitted. Medical personnel, for example, should have reasonable assurance that they can perform their procedures without unnecessary risk of exposure to such infectious diseases, and without requiring time-consuming steps to render used syringes safe for subsequent handling.

Some examples of prior art syringes that utilize needle guards are shown in U.S. Pat. Nos. 2,550,394, 2,551,339, 2,566,428, 2,607,341, 4,365,626, 4,778,453, 4,782,841, 5,064,419 and 5,088,985. However, none of these patents teach the use of the plunger as a needle guard after the syringe has been used. U.S. Pat. No. 5,064,419 has a retractable needle that is displaced into the syringe barrel and piston following use of the syringe. U.S. Pat. No. 5,088,985 discloses an arrangement in which a needle remover (28) is normally fitted within the plunger body, but which may be removed and placed over the needle to separate it from the syringe. U.S. Pat. Nos. 2,550,394, 2,551,339, 2,566,428 and 2,607,341 all disclose arrangements in which a needle guard used during shipment and handling of the syringe is removed and inserted into the barrel to serve as a plunger when the needle is ready to use. In order to reuse the plunger as a guard following its use in any of these patents would require separation of the plunger from the piston, and would require an inventive step not suggested in any of the prior art.

In addition to an effective needle guard, a means is needed to prevent sharing and reuse of syringes by intravenous drug abusers, and thereby to prevent the spread of infectious diseases caused by use of contaminated syringes. Since the major cause of spread of HIV, Hepatitis and similar diseases is through the repeated and/or shared use of contaminated hypodermic syringes and needles, a significant preventive measure would be the elimination of the ability of intravenous drug abusers to acquire syringes that could be used more than one time.

Examples of some prior art efforts to provide non-reusable syringes are disclosed in U.S. Pat. Nos. 3,478,937, 3,951,146, 4,367,738, 4,391,272, 4,493,703, 4,731,068 and 4,781,684. Most of these patented devices involve some type of catch mechanism which becomes engaged upon full or partial travel of the syringe piston to lock the piston in place and prevent either its withdrawal or its insertion into the syringe barrel. Other devices disclosed in these patents include pistons which become separated from the plunger or stem after an operating cycle to eject a fluid from the syringe. For instance, U.S. Pat. Nos. 4,391,272, 4,731,068 and 4,781,684 disclose arrangements in which both some type of catch mechanism and a separable piston and stem structure are used.

All of the prior art devices known to applicant are either excessively complicated and expensive in construction or are not adequately reliable in operation. Further, many prior art devices require either modification of the barrel, or the use of separate collars, adapters or sleeves to connect the piston to the plunger or stem. Moreover, it is possible in some of these devices to reassemble them after use, whereby they may then be repeatedly used.

Accordingly, it would be desirable to have a disposable hypodermic syringe that is reliable in operation, simple and economical in construction, and in which a part of the syringe assembly, itself, is adapted as a needle guard after the syringe has been used for its intended purpose. It would further be desirable to provide a disposable syringe that is not capable of being reused after a single use.

SUMMARY OF THE INVENTION

The disposable syringe of the invention comprises a conventional cylindrical syringe barrel having a suitable conventional fitting on one end, such as a Luer lock adapter, or other means, for attaching a needle, and an open opposite end. A plunger or stem is reciprocable in the barrel and carries a piston on its inner end for developing vacuum or pressure, depending upon the direction of reciprocation of the piston and plunger in the barrel.

An essential feature of the present invention is the use of the plunger, itself, as a guard for the needle after the syringe has been used. To this end, the plunger has a cavity formed in it, shaped to receive the needle and to remain securely attached to the syringe after it has been placed over the needle. In use, the plunger is simply removed from the barrel after the syringe has been used, and placed over the needle. There is no separate member which must be retrieved and used for this purpose. Moreover, in a preferred embodiment, a small quantity of glue is positioned in the plunger/guard to adhesively secure the plunger/guard to the needle after it is placed in operative position on the needle.

Further in accordance with the invention, the syringe is automatically rendered inoperable after a single use, so that it cannot be used again. In a conventional syringe, the piston is attached to the end of the plunger so that it will not become displaced from the plunger during use, even though the plunger and piston may be reciprocated many times in the barrel of the syringe. However, in the present invention, the piston is releasably attached to the end of the plunger by movable latch arms that move through an over center position so that the piston becomes displaced from the plunger after the plunger and piston are reciprocated through one cycle rearwardly and then forwardly in the barrel. A subsequent reciprocal movement of the plunger rearwardly in the barrel results in the piston becoming separated from the plunger so that it cannot be reattached to the plunger without the use of a special tool used during its manufacture, thus rendering the syringe incapable of further use.

In the present invention the piston is preferably made of a synthetic plastic material, whereas in conventional syringe constructions the piston is normally made of a rubber material. In an alternate construction, however, the piston used in the system of the invention may be made of rubber and still incorporate the novel features of the invention.

BRIEF DESCRIPTION OF THE DRAWINGS

The foregoing and other objects and advantages of the invention will become apparent from the following detailed description when considered in conjunction with the accompanying drawings, wherein like reference characters refer to like parts throughout the several views, and wherein.

DETAILED DESCRIPTION OF THE PREFERRED EMBODIMENTS

Figure 1:
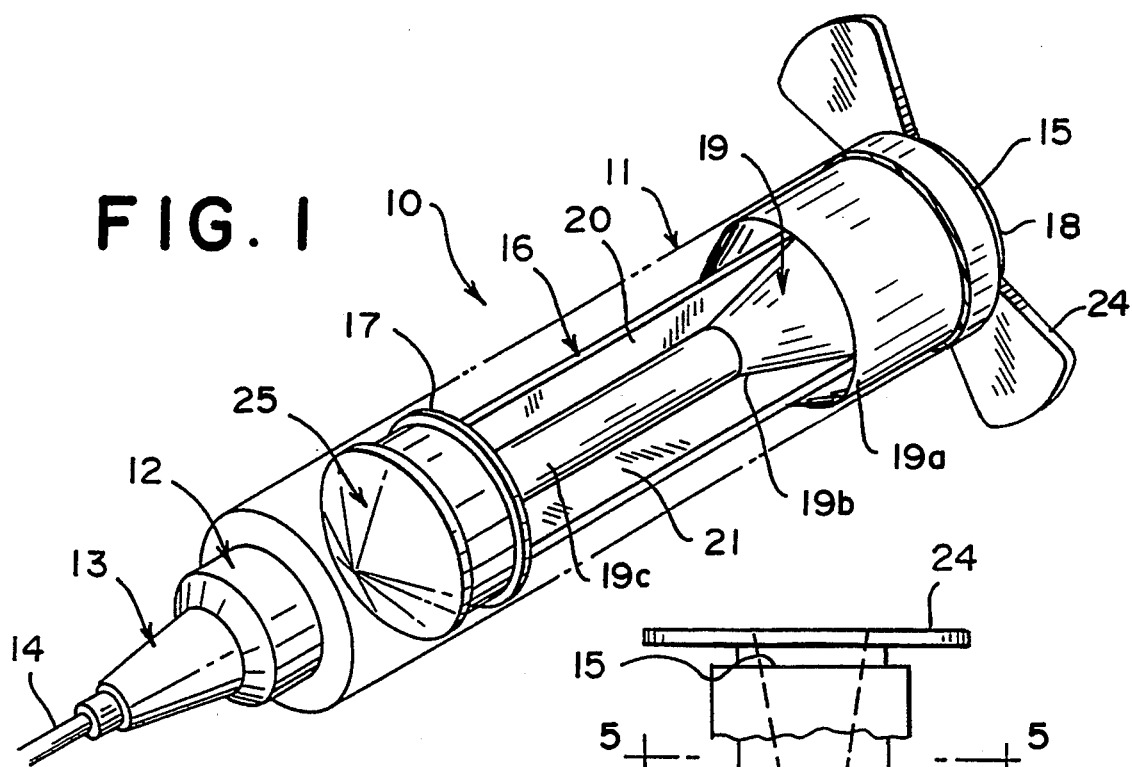
FIG. 1 is an enlarged perspective view of a syringe incorporating the built-in needle guard feature of the invention.
Figure 2:
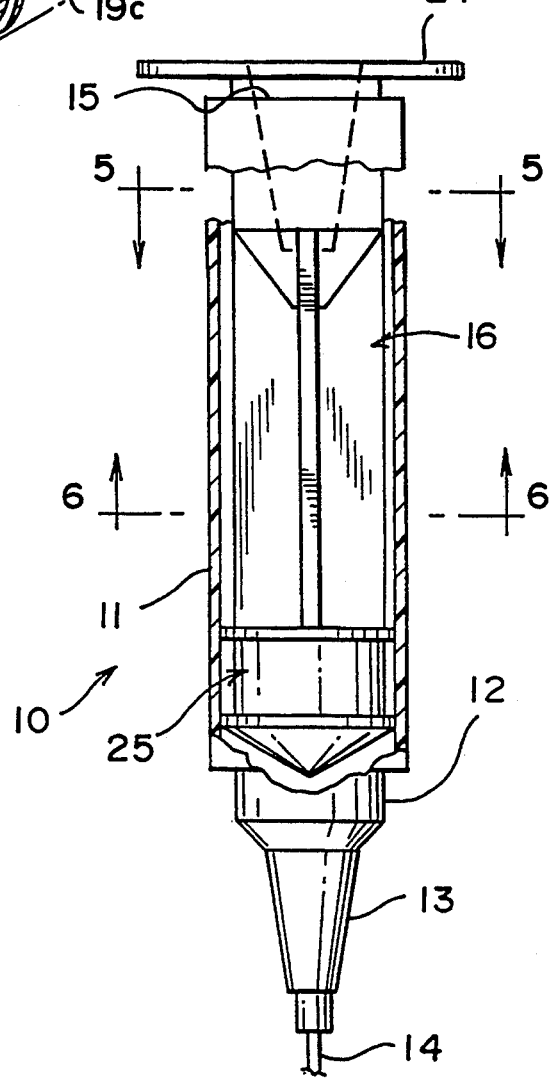
FIG. 2 is a view in elevation of the syringe of FIG. 1.

Referring more specifically to the drawings, a first form of syringe in accordance with the invention is indicated generally at 10 in FIGS. 1-6. In this form of the invention, a conventional syringe barrel 11 has a forward end 12 with a suitable means, such as a Luer lock adapter 13 for attachment of a needle 14, and an open rearward end 15.

An elongate plunger 16 is reciprocable in the barrel between a forward position inserted fully into the barrel, and a rearward position retracted or withdrawn in the barrel, and has a forward end 17 and rearward end 18. In this form of the invention, the plunger may have a generally X-shaped transverse cross-section, with a central body 19 and oppositely extending flanges 20, 21, 22 and 23 along diametrically opposite sides edge of the body to slidably support the plunger in the barrel. The rearward end of the plunger has a radially enlarged, generally bow-tie-shaped operating flange 24 which may be gripped with the fingers and used to reciprocate the plunger in the barrel, and a piston 25 is secured on the forward end of the plunger. The piston may either be releasably attached to the plunger, as in the later-described forms of the invention, or it may be permanently attached thereto as in conventional syringe constructions.

An essential feature of the present invention is the construction of the body 19 so that it is hollow and has a stepped configuration, including a larger cylindrical entry portion 19a adapted to snugly receive the forward end 12 of the syringe barrel, an intermediate tapered portion 19b adapted to lock onto the Luer Lock fitting 13 of the syringe barrel, and a reduced diameter portion 19c adapted to closely receive the needle 14.

Figure 3:
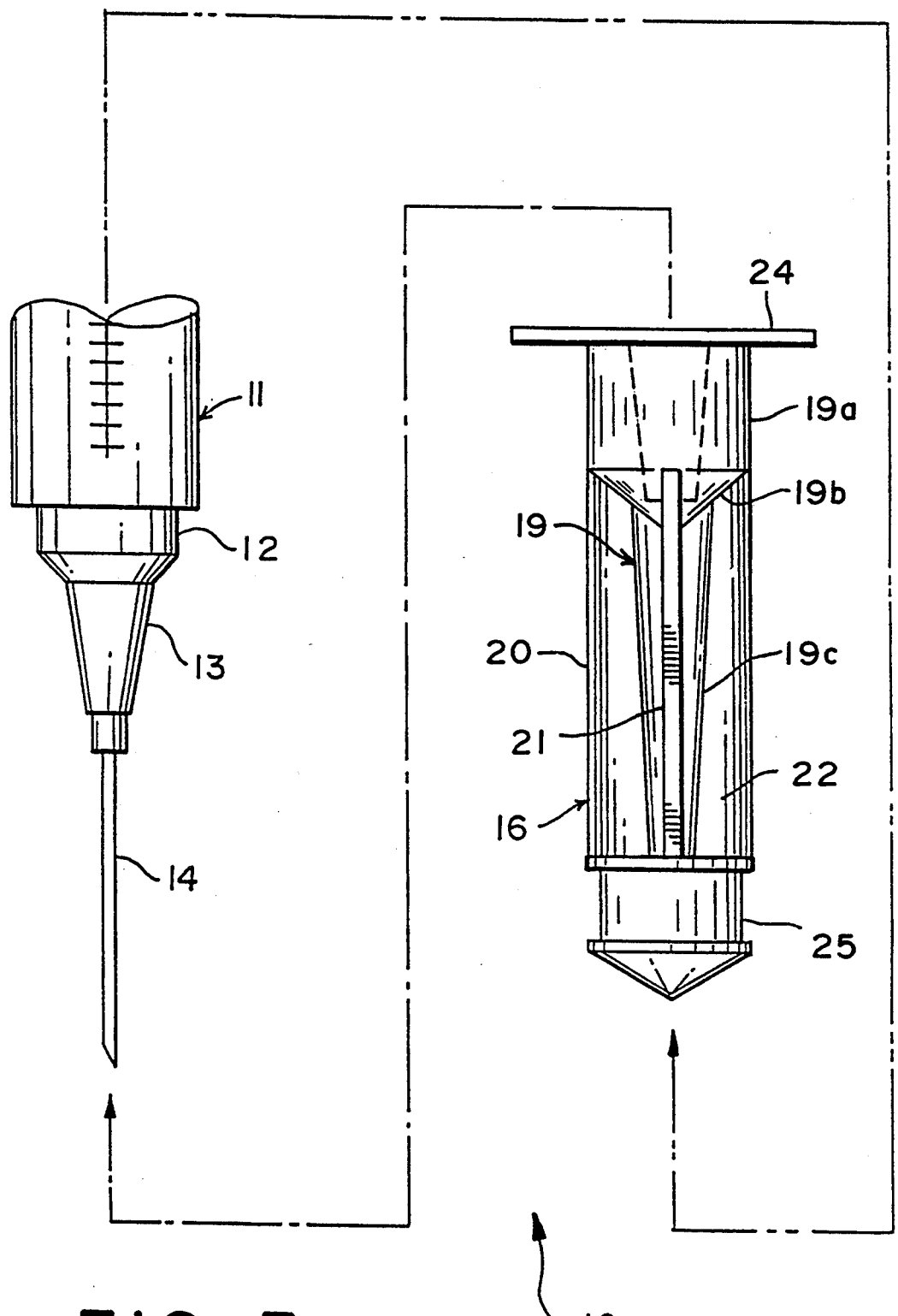
FIG. 3 is an exploded view, with parts broken away, of the syringe of FIG. 1, showing the plunger removed from the barrel and depicting how the plunger may be placed over the exposed needle to serve as a needle guard.
Figure 4:
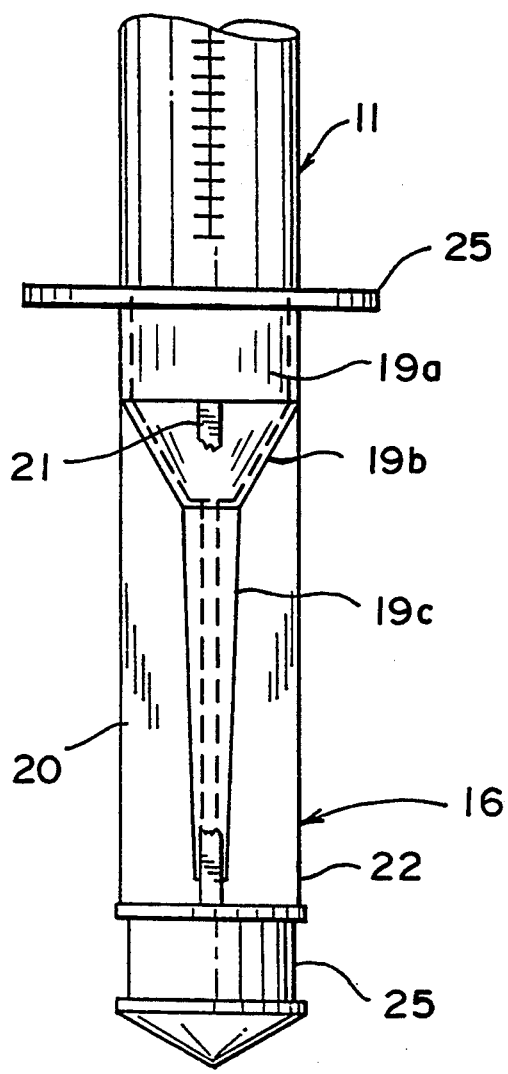
FIG. 4 is an enlarged view in elevation of the syringe of FIG. 1, showing the plunger removed from the barrel and applied to the end of the barrel to form a sheath for the needle.
Figure 6:
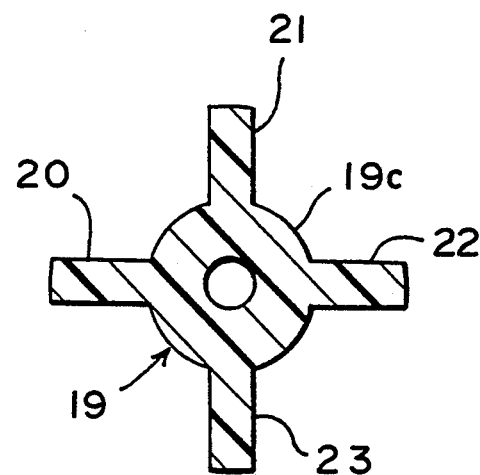
FIGS. 5 and 6 are transverse sectional views taken along lines 5—5 and 6—6, respectively, in FIG. 2.
Figure 5:
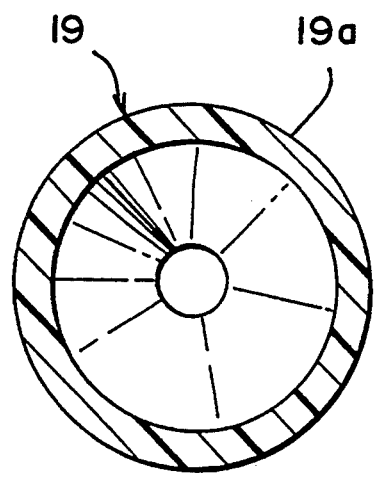

After the syringe 10 has been used, it is a simple matter for the doctor, nurse or other medical personnel to simply withdraw the plunger 16 from the barrel 11 and place the plunger over the needle, with the tapered portion 19b locking onto the Luer Lock adapter 13 of the syringe barrel, as shown in FIGS. 3 and 4. There is no need for the doctor, nurse or other person using the syringe to search for and retrieve a separate needle guard, as is presently necessary in the prior art.

Figure 7:
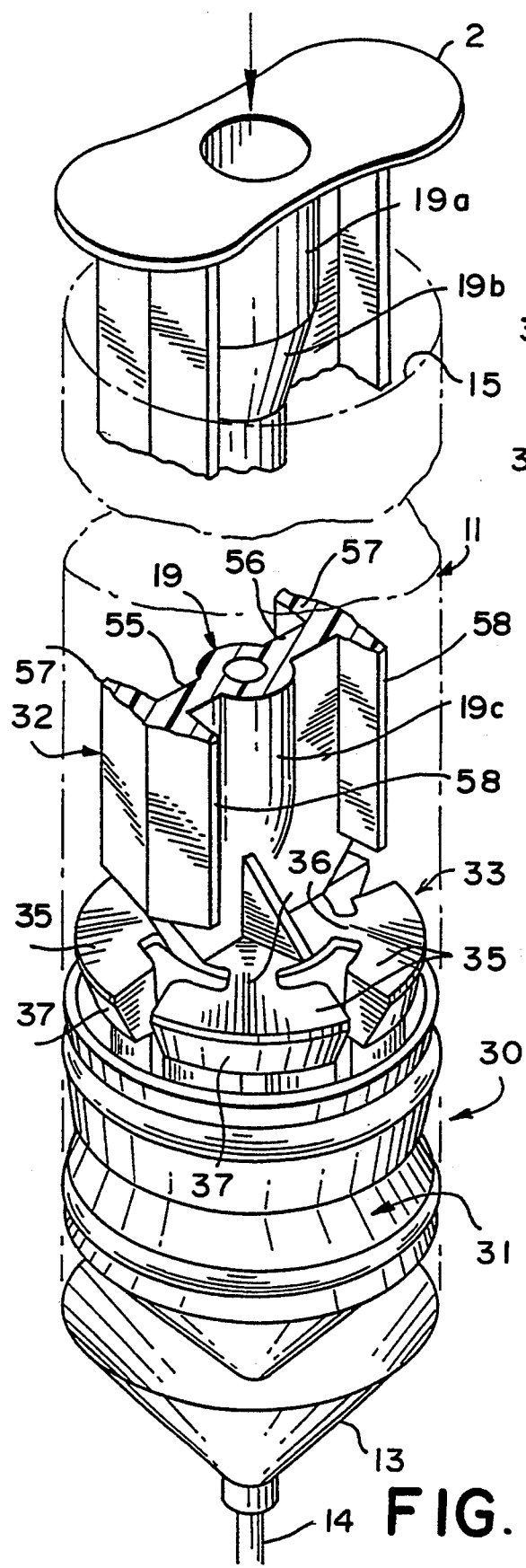
FIG. 7 is a greatly enlarged perspective view, with portions shown in section and portions broken away, of a syringe assembly incorporating both the built-in needle guard of FIG. 1 and an automatically separable piston and plunger arrangement to render the syringe incapable of reuse after a single use.
Figure 8:
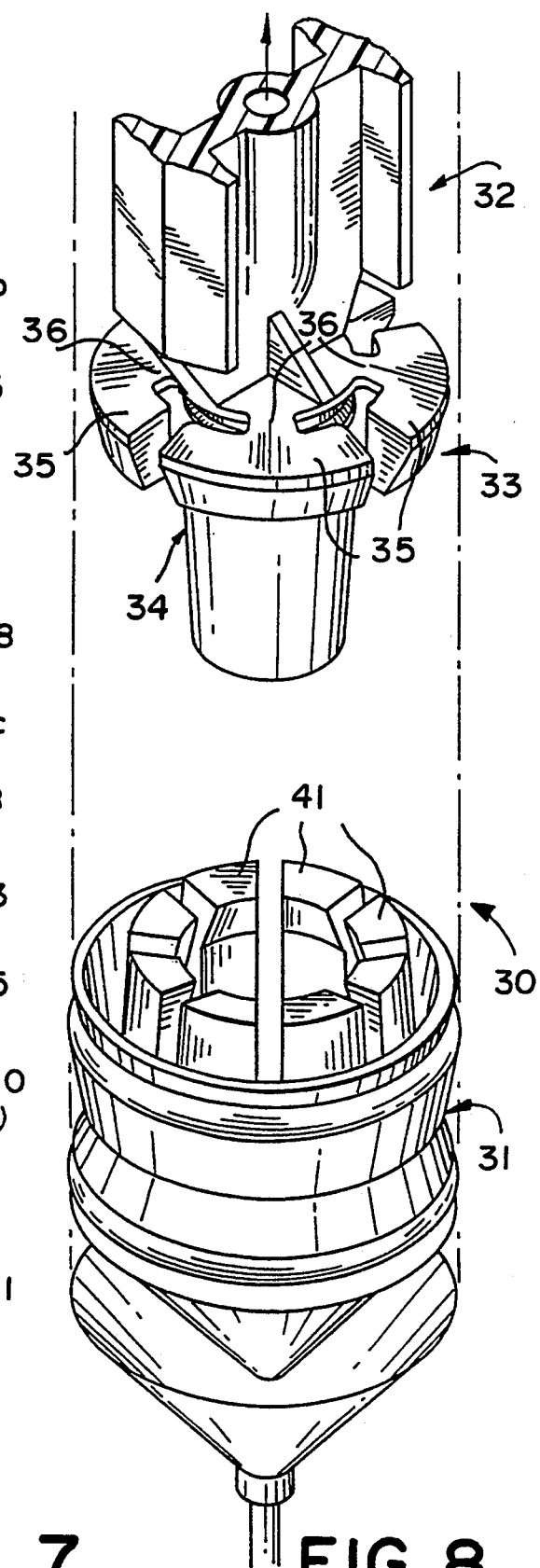
FIG. 8 is an enlarged, exploded, fragmentary perspective view of the automatically detachable piston and associated end of the plunger in the form of the invention shown in FIG. 7.
Figure 9:
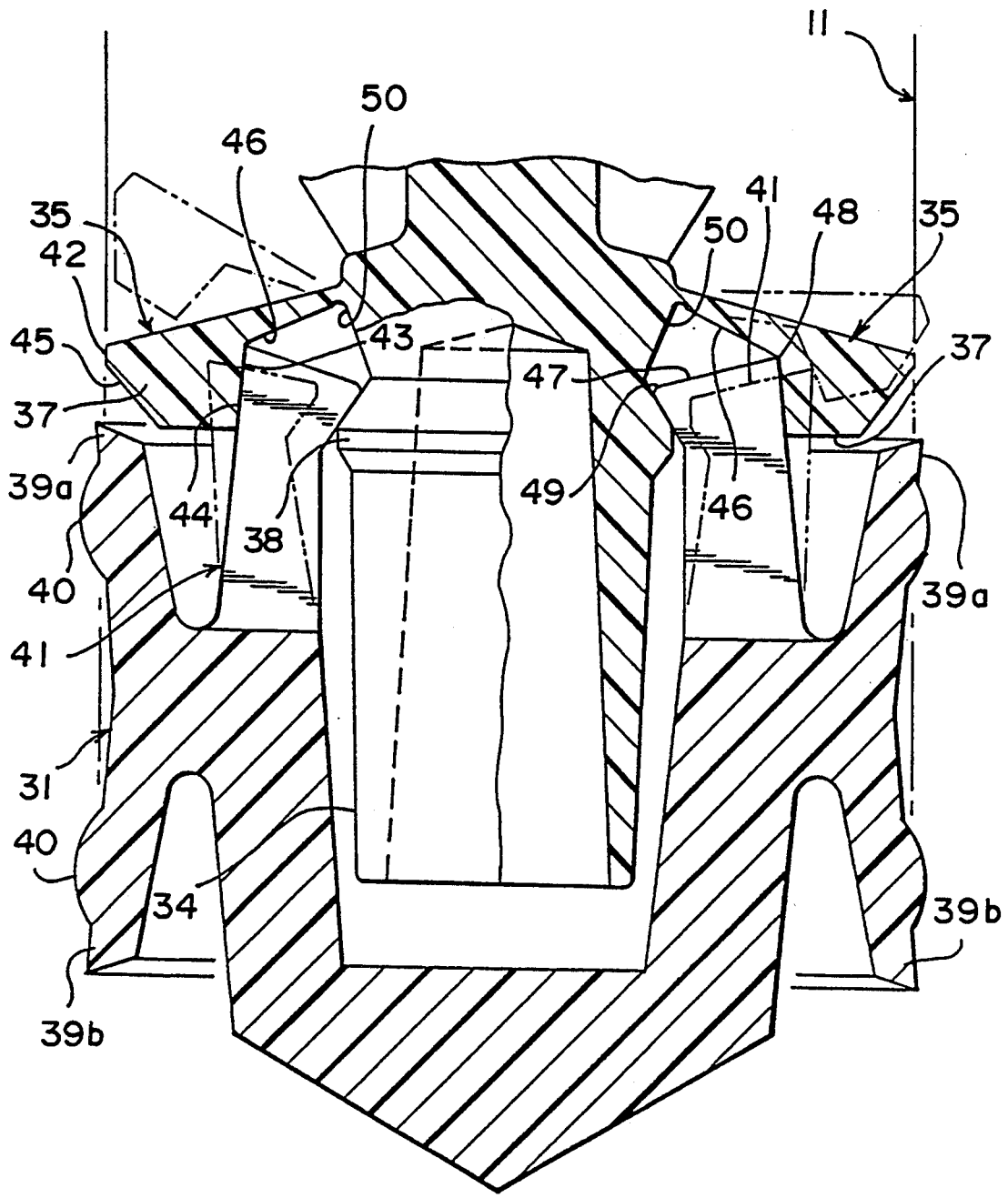
FIG. 9 is a greatly enlarged vertical sectional view of the piston and forward end of the plunger in the form of the invention shown in FIG. 7.

A second form of the invention is indicated generally at 30 in FIGS. 7-9. In this form of the invention, a detachable piston 31 is carried on the forward end of plunger 32 by an automatically releasable latching mechanism 33.

The forward end of the plunger has a reduced transverse dimension and defines an elongate, forwardly extending attaching post 34 with a plurality of radially outwardly projecting latching arms 35 integrally pivotally connected to the post at hinge areas 36. Four such latching arms are shown in the specific example described herein, but it is contemplated that a different number of arms could be used, if desired.

Each arm includes a thickened outer end portion defining detents 37 that are arranged in outwardly spaced, confronting relationship to a radially outwardly projecting retaining ring 38 formed on the post forwardly of the point of attachment of the arms to the post.

The piston 31 is carried on the post 34 at the forward end of the plunger, and as shown in FIGS. 7-9, is made of a synthetic plastic material. This plastic piston has a pair of oppositely axially projecting sealing flanges 39a and 39b, each flared radially outwardly and having a radially enlarged sealing bead 40 thereon for effecting a sliding seal with the inner surface of the barrel. Thus, during forward motion of the piston in the barrel, pressure of fluid in the barrel acting under the sealing flange 39a causes that flange to expand radially outwardly, making a tight sliding seal with the inner surface of the barrel. Conversely, rearward movement of the piston in the barrel causes lowered pressure in the forward end of the barrel to pull the sealing flange 39b outwardly to effect a tight sliding seal with the inner surface of the barrel.

The piston is held on the forward end of the plunger by a plurality of detents 41 on the end of the piston adjacent the plunger, spaced radially inwardly from the sealing flange 39a, and clamped between the latching arms 35 and retaining ring 38. These detents are molded with a natural, unbiased position as shown in FIG. 8, spaced radially outwardly out of contact with the retaining ring 38, and in the operative position of the invention are held inwardly behind the retaining ring by the latching arms 35.

As seen best in FIGS. 8 and 9, the outer ends of the arms 35, the retaining ring 38 and the detents 41 are uniquely shaped to cooperate with one another and with the inner surface of the barrel during reciprocal movement of the plunger in the barrel to either maintain the piston latched to the plunger, or to disengage the piston from the plunger.

With particular reference to FIG. 9, a first of these surfaces 42 defines a relatively narrow annular cylindrical band around the outer perimeter of the latching arms, which is parallel to the inner surface of the barrel and is adapted to slide along the inner barrel surface when the arms are in their normal, operatively latched position with respect to the detents on the piston. Thus, with the piston beginning in its forwardmost position at the forward end of the syringe, as seen in FIG. 7, this surface 42 is in parallel, sliding contact with the inner surface of the barrel.

At the same time, a second, latching surface 43 on a radially inner portion of each latching arm is in parallel, mating contact with a complemental latching surface 44 on an upper outer end portion of the detents 41 on the piston to hold the detents inwardly behind the retaining ring 38 and therefore latch the piston to the plunger, as shown in FIGS. 7 and 9.

After the piston and plunger have been withdrawn in the barrel, .and forward motion thereof is then initiated, the frictional drag between the outer ends of the latching arms and the inner surface of the barrel causes the arms to pivot rearwardly, as depicted in dashed lines in FIG. 9, through an over-center position to a rearwardly flexed inoperative position. The over center action results from the difference in diameter of the latching arms in comparison with the diameter of the inner surface of the barrel. Thus, when the arms are in their latched, operative position as shown in full lines in FIG. 9, the first surface 42 is on essentially the same diameter as the inner diameter of the barrel, and this surface is in close, sliding contact with the inner surface of the barrel. However, when the arms pivot rearwardly upon forward movement of the piston in the barrel, the outer ends thereof swing through an arc that places the outer ends of the arms on a greater diameter than the diameter of the inner surface of the barrel. Continued forward movement of the piston in the barrel results in the arms pivoting to their unlatched position shown in dashed lines at the left hand side of FIG. 9. In this position, a third surface 45 on the outer end of the latching arms is in parallel, sliding contact with the inner surface of the barrel. This surface 45 has substantial width in relationship to the first surface 42, and maintains the latching arms in this unlatched position, regardless of the direction of motion of the piston in the cylinder.

The operating relationship between a fourth surface 46 on the underside of the latching arm and the upper end of the detents 41 will become apparent. The upper end of the detents has a slightly tapered surface 47 that extends between a heel 48 at the radially outermost end thereof, to a nose 49 at the innermost end. Thus, when the plunger and piston have been retracted in the barrel, and forward motion thereof is then initiated, the heel 48 begins pushing upwardly against surface 46 on the latching arm, and, combined with the frictional drag of the Outer end of the arm against the inner surface of the barrel, begins upward flexing movement of the arm. Continued movement in this direction causes the nose 49 to begin sliding upwardly along a fifth surface 50 on the post immediately below the point of attachment of the arms, resulting in radially outward pivoting movement of the detents and continued upward pushing action of the heel against the surface 46. The latching arms are thus pivoted completely through this "overcenter" motion to their fully unlatched position shown in dashed lines on the left side of FIG. 9, where the end surface 47 on the detents is in parallel contact with the undersurface 46 of the latching arms, securely holding the latching arms in their unlatched position during downward movement of the plunger and piston in the barrel and providing a large contact area between the plunger and piston for pushing the piston forwardly in the barrel.

When the plunger is again retracted in the barrel, the surfaces 45 on the outer ends of the latching arms easily slide along the inner surface of the barrel, whereby the latching arms are maintained in their unlatched position, regardless of the direction of reciprocation of the plunger in the barrel.

Upon subsequent withdrawal of the plunger in the barrel, the unlatched piston remains in its forwardmost, previously pushed position in the barrel.

During assembly of the syringe of the invention, the piston is first inserted into the barrel through the open rearward end thereof, and the plunger is next inserted to bring the post and latching arms into juxtaposition with the piston. A special tool (not shown) is then inserted through the open end of the barrel and into contact with the latching arms, and is used to force the latching arms through their over-center position into the latched position shown in FIG. 9.

The plunger 32 in this form of the invention also has a hollow central body 19, as in the previous form of the invention, with stepped diameter portions 19a, 19b and 19c for the same purposes as described in connection with the previous embodiment. However, rather than the X-shaped cross-section as previously described, the plunger in this form of the invention has a pair of laterally projecting webs 55 and 56 with oppositely directed circumferentially extending flanges 57 and 58 on their outer edges. In all other respects, and with the two exceptions noted above, this form of the invention functions the same and has all the advantages of the previous form of the invention.

Figure 10:
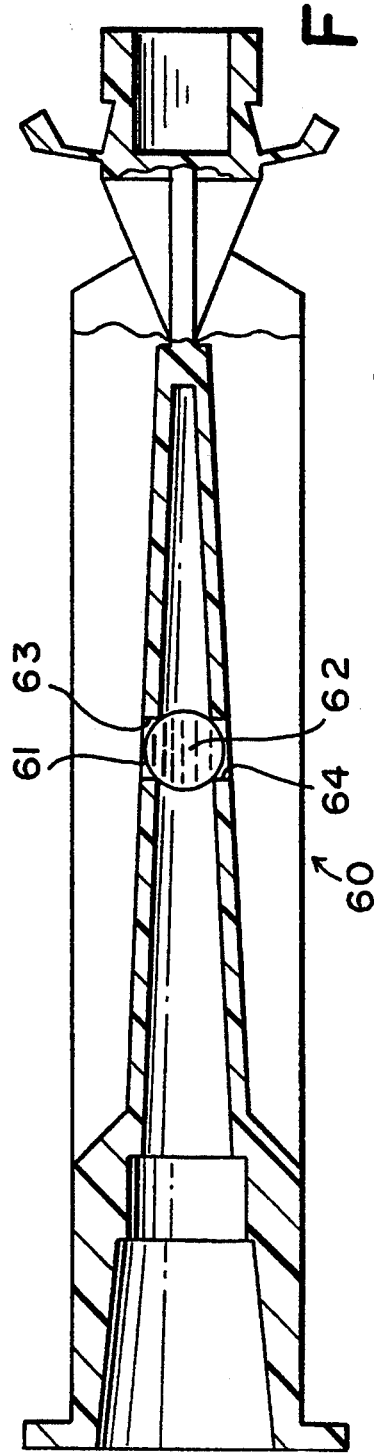
FIG. 10 is an enlarged, longitudinal sectional view of the plunger in a further modified form of the invention, wherein a small envelope containing an adhesive is placed in the bore of the plunger to adhesively secure the plunger/guard to the needle after the syringe has been used for its intended purpose.
Figure 11:
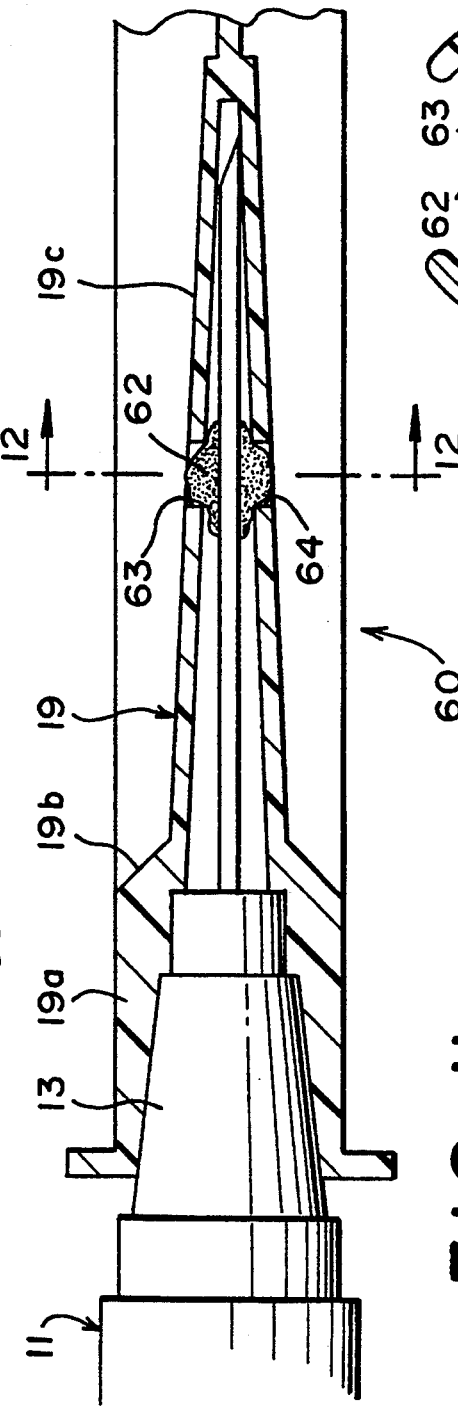
FIG. 11 is a view similar to FIG. 10, showing how the adhesive-containing envelope is pierced by the needle when the plunger is placed in operative relationship over the needle.
Figure 12:
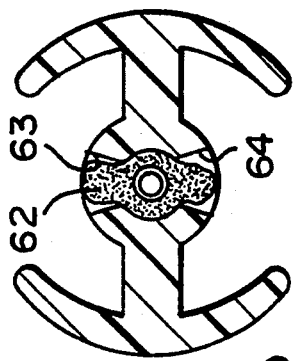
FIG. 12 is a transverse sectional view, taken along line 12—12 in FIG. 11, showing how the adhesive forms a mechanical lock with the needle in the plunger bore after the envelope is pierced with the needle.

A further form of the invention is indicated generally at 60 in FIGS. 10-12. This form of the invention is essentially the same as that form illustrated in FIGS. 7-9. However, in this form a small envelope 61 containing an adhesive 62 is located in the hollow bore portion 19c of the syringe in a position to be pierced by the needle 14 as the plunger is placed over the needle. The envelope 61 is roughly the size of a BB and is located at a point in the bore where small openings 63 and 64 are formed during the molding process. When the needle pierces the envelope, the adhesive 62 escapes and flows into the space surrounding the needle and into the two small openings 63 and 64, thereby forming a mechanical lock between the needle and the plunger and preventing removal of the plunger after the adhesive has cured. It should also be noted that it is anticipated that a small quantity of the adhesive will enter the end of the needle as it passes through the envelope of adhesive, plugging the needle and preventing its use even if access to it should be gained.

Figure 13:
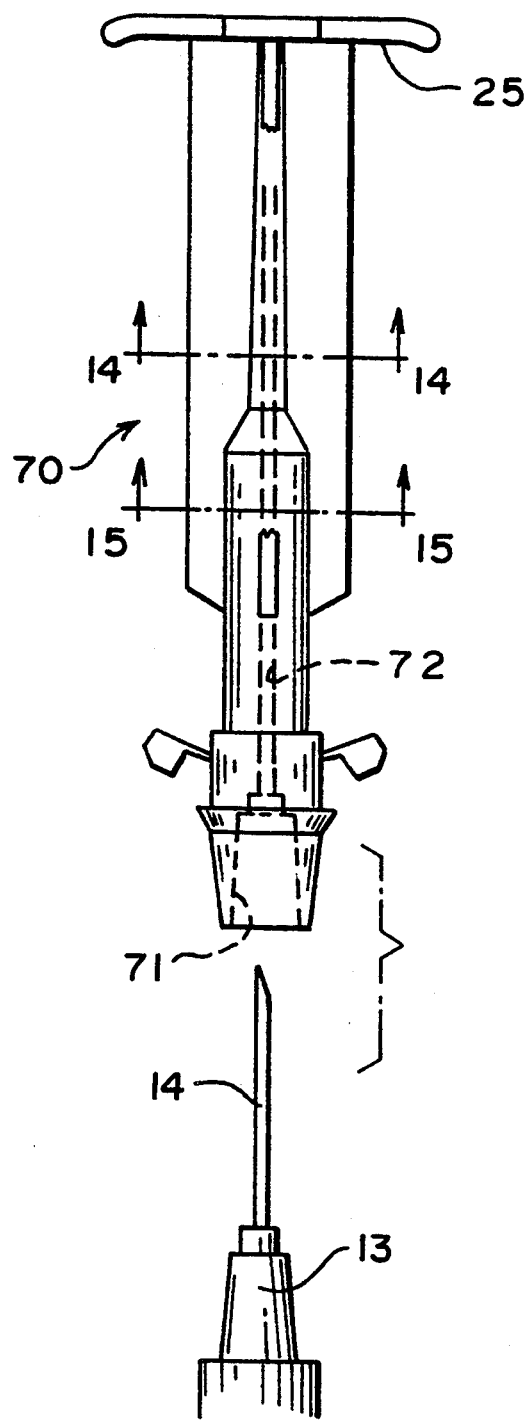
FIG. 13 is an exploded view in elevation of another form of the invention, wherein the forward end of the plunger from which the piston has become separated is inserted over the needle.
Figure 14:
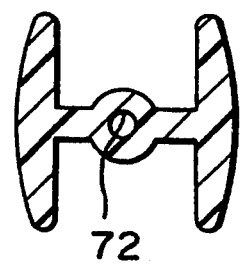
FIGS. 14 and 15 are transverse sectional views taken along lines 14—14 and 15—15, respectively, in FIG. 13.
Figure 15:
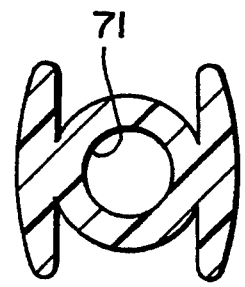

Yet another modification of the invention is indicated generally at 70 in FIGS. 13-15. In this form of the invention, the piston-receiving end 17 of the plunger is shaped with a tapered recess 71 for locking engagement on the Luer Lock adapter 13 of the syringe barrel, and a reduced diameter elongate opening 72 extends from the end of the tapered section to receive the needle 14. The major difference between this form of the invention and that previously described is that the plunger may be grasped by the flanged end 25, pulled from the syringe barrel, and pushed over the needle without inverting it end-for-end.

While the piston has been described herein as made of plastic, it should be understood that it may equally as well be made of rubber, as described in copending application Ser. No. 07/802,628. In such event, the piston itself is constructed differently in the area where it seals with the barrel, but the latching mechanism is substantially identical to that previously described, and the hollow body for encasing the needle are the same as before.

In a specific example of the invention, and with the latching arms in their natural, as-molded position, the first surface 42 is disposed at an angle of 15° relative to the longitudinal axis of the syringe, the third surface 45 is disposed at an angle of 25° relative to the longitudinal axis, and the fourth surface 46 is inclined 20° with respect to the transverse axis of the syringe. Further, there are four substantially uniformly circumferentially spaced latching arms and eight substantially uniformly circumferentially spaced detents, with each latching arm arranged to press against two of the detents.

The syringe of the invention is simple and economical in construction, and does not require any more parts than a conventional syringe, i.e., the barrel, plunger and piston. Yet, it provides an entirely different structure and function as compared with a conventional syringe, i.e., the plunger doubles as a needle guard after the syringe has been used. Further, as described in somewhat greater detail in the parent application, the piston is connected to the plunger through a latched construction that automatically disables the syringe after a single use.

While the invention has been illustrated and described in detail herein, it is to be understood that various modifications may be made therein without departing from the spirit and scope of the invention, as defined by the appended claims.

What is claimed is:

1. A non-reusable syringe having a built-in needle guard, comprising:
   an elongate cylindrical barrel having adapter means on one end for attachment of a needle, and an open other end;
   a needle secured to said adapter means on said one end of the barrel;
   an elongate plunger reciprocable in the barrel between a forward position in the barrel and a retracted position, said plunger having a forward end in the barrel and a rearward end accessible exteriorly of the barrel for operating the plunger;
   a piston carried on the forward end of the plunger for effecting a sliding seal with the barrel to draw material into the barrel and discharge it therefrom through said one end upon reciprocating motion of the plunger and piston in the barrel;
   said plunger having a hollow bore formed longitudinally through a central portion thereof, said bore including a first portion for cooperative locking engagement with the adapter means on the barrel and a second portion for receipt of the needle, whereby the plunger may be withdrawn from the barrel and placed in shielding relationship over the needle after the syringe has been used for its intended purpose; and
   a small ampoule piercable by the needle and containing a quantity of liquid adhesive that cures in the presence of oxygen located in the second portion of the hollow bore in position to be pierced by the needle when the plunger is removed from the barrel and placed over the needle, said adhesive serving to adhesively secure the plunger over the needle in shielding relationship thereto.

2. A syringe as claimed in claim 1, wherein:
   the plunger has small openings in a sidewall thereof adjacent the location of the ampoule of adhesive, whereby when the ampoule is pierced the liquid adhesive will flow into the openings prior to curing and thereby form a mechanical lock between the adhesive, needle and plunger after the adhesive cures.

3. A syringe as claimed in claim 1, wherein:
   the bore is formed in the plunger from the rearward end thereof, and terminates in a distal, closed end of the second portion.

4. A syringe as claimed in claim 1, wherein:
   the piston is detachably connected to the plunger by releasable latch means that automatically disengages when the piston and plunger are reciprocated through one complete cycle of operation rearwardly and forwardly in the barrel.

5. A syringe as claimed in claim 4, wherein:
   the bore is formed in the plunger from the forward end thereof, and terminates in a distal, closed end of the second portion, and wherein detachment of said piston from said plunger exposes said bore so that the plunger may be used as a needle guard.

6. A syringe as claimed in claim 1, wherein:
   releasable latching means are on the piston and plunger for latching the piston to the plunger during initial retraction of the plunger and piston in the barrel, and for unlatching the piston from the plunger during forward movement thereof, so that the piston becomes disengaged from the plunger during subsequent retraction of the plunger in the barrel, said latching means including latching arms carried on the forward end of the plunger and extending radially outwardly into sliding contact with an inner surface of the barrel, said latching arms having a first position in latching engagement with detent means on the piston to retain the piston on the plunger, and being movable to a second, overcenter, unlatched position releasing the piston from the plunger.

7. A syringe as claimed in claim 6, wherein:
   the latching arms have latching surfaces thereon normally engaged with detents on the piston to urge the detents into latching engagement with a retaining ring on the plunger, whereby the detents on the piston are normally gripped between the latching arms and the retaining ring to retain the piston on the plunger.

8. A syringe as claimed in claim 7, wherein:
   the latching arms are adapted to slide along the inner surface of the barrel in their latched position during rearward movement of the plunger in the barrel, but sliding friction between the latching arms and the barrel during forward movement of the plunger in the barrel causes the arms to move to their overcenter, unlatched position.

9. A syringe as claimed in claim 8, wherein:
   the bore is formed in the plunger from the forward end thereof, and terminates in a distal, closed end of the second portion, and wherein detachment of said piston from said plunger exposes said bore so that the plunger may be used as a needle guard.

10. A syringe as claimed in claim 8, wherein:
    the bore is formed in the plunger from the rearward end thereof, and terminates in a distal, closed end of the second portion.

11. A syringe as claimed in claim 1, wherein:
    the piston is made of plastic.

* * * * *